United States Patent
Myers

(10) Patent No.: US 11,192,840 B2
(45) Date of Patent: Dec. 7, 2021

(54) METHOD FOR RECYCLING CATALYST IN THE PRODUCTION OF CHLORINATED ALKANES

(71) Applicant: Blue Cube IP LLC, Clayton, MO (US)

(72) Inventor: John D. Myers, Clayton, MO (US)

(73) Assignee: Blue Cube IP LLC, Clayton, MO (US)

( * ) Notice: Subject to any disclaimer, the term of this patent is extended or adjusted under 35 U.S.C. 154(b) by 0 days.

(21) Appl. No.: 16/981,976

(22) PCT Filed: Apr. 2, 2019

(86) PCT No.: PCT/US2019/025334
§ 371 (c)(1),
(2) Date: Sep. 17, 2020

(87) PCT Pub. No.: WO2019/195248
PCT Pub. Date: Oct. 10, 2019

(65) Prior Publication Data
US 2021/0009490 A1    Jan. 14, 2021

Related U.S. Application Data

(60) Provisional application No. 62/652,107, filed on Apr. 3, 2018.

(51) Int. Cl.
| | | |
|---|---|---|
| *C07C 17/275* | (2006.01) | |
| *C07C 17/278* | (2006.01) | |
| *C07C 19/01* | (2006.01) | |
| *B01J 23/745* | (2006.01) | |
| *C07C 17/383* | (2006.01) | |
| *C07C 17/395* | (2006.01) | |
| *C07C 17/38* | (2006.01) | |
| C07C 19/08 | (2006.01) | |
| C07C 21/06 | (2006.01) | |
| C07C 21/08 | (2006.01) | |

(52) U.S. Cl.
CPC ........... *C07C 17/275* (2013.01); *B01J 23/745* (2013.01); *C07C 17/278* (2013.01); *C07C 17/38* (2013.01); *C07C 17/383* (2013.01); *C07C 17/395* (2013.01); *C07C 19/01* (2013.01); *C07C 19/08* (2013.01); *C07C 21/06* (2013.01); *C07C 21/08* (2013.01); *Y02P 20/584* (2015.11)

(58) Field of Classification Search
CPC ..................................................... C07C 17/281
See application file for complete search history.

(56) References Cited

U.S. PATENT DOCUMENTS

2003/0199716 A1* 10/2003 Wilson .................... C07C 19/01
570/262

FOREIGN PATENT DOCUMENTS

| WO | 2009085862 | 7/2009 |
|---|---|---|
| WO | 2015058566 | 4/2016 |

OTHER PUBLICATIONS

International Search Report dated Jun. 24, 2019, PCT/US2019/025334.
Written Opinion of the International Searching Authority dated Jun. 24, 2019, PCT/US2019/025334.

* cited by examiner

*Primary Examiner* — Medhanit W Bahta
(74) *Attorney, Agent, or Firm* — Polsinelli PC

(57) ABSTRACT

The present invention provides highly efficient processes for the preparation of chlorinated alkanes. The processes comprise contacting an alkene, halogenated alkene, or combinations thereof, a halogenated methane comprising at least one chlorine atom, at least one solid metallic catalyst, and a ligand forming a reaction mixture in a reactor. The product mixture does not contain a phase transfer catalyst. After a product mixture is formed, various fractions, distillation streams, and effluent streams are separated and/or treated with an aqueous alkaline substance. This treatment removes at least a portion of the metal and through recycling of the heavy fraction, treated product mixture, or combinations thereof, allows for the kinetics of the process to be maintained or increased.

31 Claims, 1 Drawing Sheet

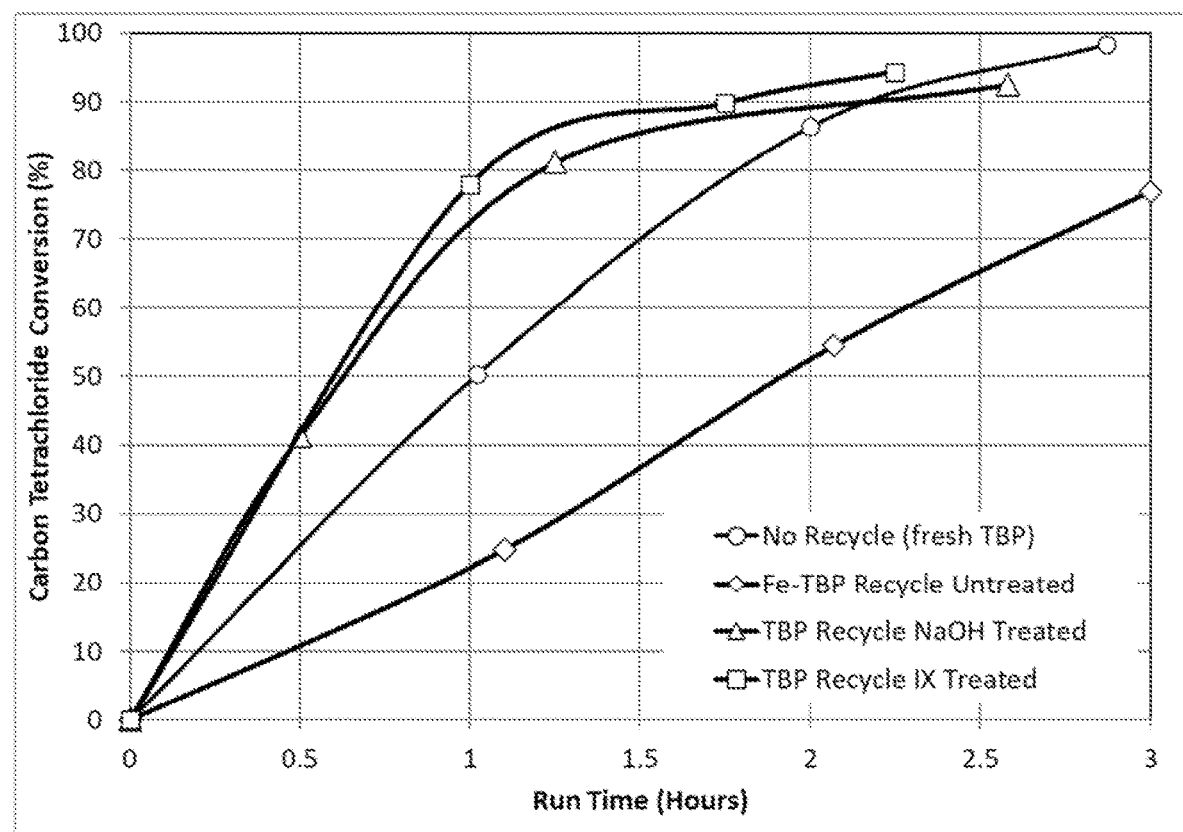

METHOD FOR RECYCLING CATALYST IN THE PRODUCTION OF CHLORINATED ALKANES

CROSS-REFERENCE TO RELATED APPLICATIONS

This application is a national stage entry of PCT/US2019/025334 filed Apr. 2, 2019, which claims the benefit of U.S. Provisional application 62/652,107 filed Apr. 3, 2018, each of said applications are expressly incorporated herein by reference in their entirety.

FIELD OF THE INVENTION

The present disclosure generally relates to processes for preparing chlorinated alkanes.

BACKGROUND OF THE INVENTION

Chlorinated alkanes are useful intermediates for many products including agricultural products, pharmaceuticals, cleaning solvents, solvents, gums, silicones, and refrigerants. The processes to prepare chlorinated alkanes can be time consuming, moderately efficient, and lack reproducibility.

One subset of chlorinated alkanes which have been shown to be useful are chlorinated propanes such as 1,1,1,3-tetrachloropropane, 1,1,1,3,3-pentachloropropane, and 1,1,1,3,3,3-hexachloropropane. These chlorinated propanes are useful intermediates for many products in the chemical, pharmaceutical, and agriculture area. One area which utilizes these chlorinated propane intermediates extensively is in preparation of refrigerants.

A few manufacturing processes have been developed to efficiently prepare chlorinated propanes on scale. A general telomerization process for their preparation consists of contacting an alkene, carbon tetrachloride, a trialkylphosphate, and an iron catalyst. One patent, U.S. Pat. No. 4,650,914, teaches such a process where the process is conducted in batch mode, using a non-powder form of an iron and mechanical stirring. Further processes extend this technology such as U.S. Pat. Nos. 6,313,360 and 8,907,147 where these patents disclose a continuous process using a powdered form of iron and mechanical stirring. In each of these cases, the kinetics of the process are reduced due to poisoning of the catalyst which further causes impurities to be formed. One process disclosed, JP 2017178897, discloses processes for the preparation of chlorinated propanes where an identified impurity was described as an insoluble metal complex of iron. In order to remove this insoluble metal complex, the reaction contents were washed with an aqueous acid. This patent indicated that the catalyst becomes deactivated during the process. WO 2016058566 describes a process for the production of chlorinated propanes. This application discloses the degradation of catalyst during the isolation of the product.

In each of the above, while the processes can be moderately efficient, they suffer from reduced the kinetics and are less efficient. Developing a process that can prepare halogenated alkanes, such as chlorinated propanes, where the process exhibits high kinetics, is reproducible, provides improved yields, utilizes various recycling strategies, and affords greater through-put, would be advantageous.

SUMMARY OF THE INVENTION

In one aspect, disclosed herein are processes for preparing chlorinated alkanes. The processes comprising:

(a) contacting at least one alkene, chlorinated alkene, or combinations thereof, a halogenated methane comprising at least one chlorine atom, at least one solid metallic catalyst, and a ligand to form a reaction mixture in a reactor;

(b) forming a product mixture comprising a chlorinated alkane, light by-products, heavy by-products, soluble metal ions, complexes of metal ions with the ligand, or combinations thereof;

(c) optionally distilling at least a portion of the product mixture to form a distilled product mixture;

(d) treating at least a portion of the product mixture from step (b) and/or the distilled product mixture from step (c) with an alkaline substance in the absence of a phase transfer catalyst, to form a treated product mixture and/or treated distilled product mixture; wherein the alkaline substance is insoluble in the treated product mixture or the treated distilled product mixture; wherein the alkaline substance reacts with at least some of the metal ions that are present and forms a metal hydroxide; and wherein the treated product mixture and/or the treated distilled product mixture contains fewer metal ions than the product mixture from step (b);

(e) separating the metal hydroxide from the treated product mixture and/or the treated distilled product mixture to form a treated product effluent stream and/or a treated distilled effluent stream;

(f) optionally distilling the treated product effluent stream and/or the treated distilled effluent stream of step (e) to form the final treated product stream and/or the final treated distilled product stream; and (g) recycling at least a portion of at least one of the distilled product mixture from step (c), treated product effluent stream and/or a treated distilled effluent stream from step (e), the final treated product stream and/or the final treated distilled product stream from step (f), to the reactor.

The above separation and/or treatment steps help to ensure the catalyst does not degrade or become poisoned, and thereby help to maintain the kinetics of the reaction.

(a) contacting at least one alkene, chlorinated alkene, or combinations thereof, a halogenated methane comprising at least one chlorine atom, at least one solid metallic catalyst, and a ligand to form a reaction mixture in a reactor;

(b) forming a product mixture comprising a chlorinated alkane, light by-products, heavy by-products, soluble metal ions, complexes of metal ions with the ligand, or combinations thereof;

(c) optionally distilling at least a portion of the product mixture forming a heavy fraction and a light fraction;

(d) treating at least a portion of the product mixture from step (b) or a heavy fraction from distillation from step (c) with an alkaline substance in the absence of a phase transfer catalyst, to form a treated product mixture or treated heavy fraction stream; wherein the alkaline substance is insoluble in the treated product mixture or the treated heavy fraction stream; wherein the alkaline substance reacts with at least some of the metal ions and forms a metal hydroxide; and wherein the treated product mixture or the treated heavy fraction stream contains fewer metal ions than the product mixture;

(e) separating the metal hydroxide from the treated product mixture or the heavy fraction to form a treated product effluent stream or the treated heavy fraction stream; and (f) recycling at least a portion of the light fraction from step (c), treated product effluent stream from step (e), the treated heavy fraction stream from step (e), the light effluent stream from step (f), heavy effluent stream from step (f), or combinations thereof to the reactor. These separation and/or treatment steps help to ensure the catalyst does not degrade or become poisoned, and thereby help to maintain the kinetics at a high level.

In another aspect, disclosed herein are processes for preparing 1,1,1,3-tetrachloropropane (250FB). The process comprises the steps described above, and in step (a), ethylene, carbon tetrachloride, at least one solid metallic catalyst, and a ligand are combined to form a reaction mixture in a reactor; and the product mixture of step (b) comprises 1,1,1,3-tetrachloropropane.

In yet another aspect, disclosed herein are processes for preparing 1,1,1,3,3-pentachloropropane (240FA). The process comprises the steps described above, and in step (a) vinyl chloride, carbon tetrachloride, at least one solid metallic catalyst, and a ligand are combined to form a reaction mixture in a reactor; and the product mixture of step (b) comprises 1,1,1,3,3-pentachloropropane.

In still another aspect, disclosed herein are processes for preparing 1,1,1,3,3,3-hexachloropropane. The process comprises the steps described above, and in step (a) vinylidene chloride, carbon tetrachloride, at least one solid metallic catalyst, and a ligand are combined to form a reaction mixture in a reactor; and the product mixture of step (b) comprises 1,1,1,3,3,3-hexachloropropane.

Other features and iterations of the invention are described in more detail below.

BRIEF DESCRIPTION OF THE DRAWINGS

The present patent or application file contains at least one drawing executed in color. Copies of this patent or patent application publication with color drawing(s) will be provided by the Office upon request and payment of the necessary fee.

The FIGURE is a graphical representation showing the % conversion of carbon tetrachloride to 1,1,1,3-tetrachloropropane versus run time (hours).

DETAILED DESCRIPTION OF THE INVENTION

One aspect of the present disclosure encompasses processes for the preparation of halogenated alkanes. The processes comprise contacting at least one alkene, halogenated alkene, or combinations thereof, a halogenated methane comprising at least one chlorine atom, at least one solid metallic catalyst, and a ligand to form a reaction mixture in a reactor. The product mixture is formed comprising a chlorinated alkane, light by-products, heavy by-products, and soluble metal ions, complexes of metal ions with the ligand, or combinations thereof.

Optionally, at least a portion of the product mixture is distilled to form a distilled product mixture, which comprises at least two fractions, i.e., light and heavy fractions. In one embodiment, the light fraction is separated from the heavy fraction. Then, at least a portion of the product mixture and/or the distilled product mixture are treated with an alkaline substance in the absence of a phase transfer catalyst to form a treated product mixture and/or treated distilled product mixture. The treated product mixture and/or treated distilled product mixture contain fewer metal ions than the product mixture and/or the distilled product mixture. In one embodiment, at least a portion of the heavy fraction that was separated from the distilled product mixture is treated with an alkaline substance. After separating the iron hydroxide from the treated product mixture and/or the treated distilled product mixture, a treated product effluent stream and/or a treated distilled effluent stream are produced.

One or both of the treated product effluent stream and/or a treated distilled effluent streams is optionally distilled. In one embodiment, at least one of the treated product effluent stream and/or a treated distilled effluent stream is distilled, which affords the final treated product stream and/or the final treated distilled product stream. Other distillation streams can be formed, which may contain a variety of different materials. These other distillation streams may be lights and/or heavies. Finally, at least a portion of at least one of the distilled product mixture, the treated product effluent stream and/or a treated distilled effluent stream, the final treated product stream and/or the final treated distilled product stream, of any other distillation streams that are formed, are recycled to the reactor.

(I) Process for the Preparation of Halogenated Alkanes

One aspect of the present disclosure encompasses processes for the preparation of chlorinated alkanes. The processes comprise forming a reaction mixture comprising a halogenated methane comprising at least one chlorine atom, an alkene, halogenated alkene, or combinations thereof, and a ligand comprising at least one phosphorus containing compound comprising a trialkylphosphite, trialkylphosphate, and combinations thereof, and at least one catalyst. Once this reaction mixture is formed, the reaction mixture is stirred and heated producing chlorinated alkanes and heavy by-products are formed.

(a) Reaction Mixture

The processes commence by preparing a reaction mixture comprising an alkene, halogenated alkene, or combinations thereof, a halogenated methane comprising at least one chlorine atom, an alkene, halogenated alkene, or combinations thereof, at least one ligand, and at least one solid metallic catalyst.

(i) Alkene, Halogenated Alkene, or Combinations Thereof

A wide variety of alkenes, halogenated alkenes, or combinations thereof may be used in the process. As appreciated by the skilled artisan, the alkene, halogenated alkene, or combinations thereof may be introduced in the reaction as a liquid or a gas wherein the alkene, halogenated alkene, or combinations thereof may be at least partially soluble in the at least one halogenated methane comprising at least one chlorine atom. In various embodiments, the alkene, halogenated alkene, or combinations thereof may be introduced above the surface or below the surface of the at least one halogenated methane comprising at least one chlorine atom through a port in the reactor. Under conditions of the process as detailed below, the alkene, halogenated alkene, or combinations thereof may be liquid and then may undergo a phase transition from a liquid to a gas. As appreciated by the skill artisan, the alkene, a halogenated alkene, or combinations thereof may be introduced into the reactor to maintain the pressure with the reactor.

Generally, the alkene, halogenated alkene, or combinations thereof comprise between 2 and 5 carbon atoms. Non-limiting examples of alkenes may be ethylene, propylene, 1-butene, 2-butene, isobutene, 1-pentene, 2-pentene, 3-pentene, 2-methyl-2-butene, 2-methyl-1-butene, and 3-methyl-1-butene. Non-limiting examples of halogenated alkenes may be vinyl chloride, vinyl bromide, vinyl fluoride, allyl chloride, allyl fluoride, 1-chloro-2-butene, 1-fluoro-2 butene, 3-chloro-1-butene, 3-fluoro-1-butene, 3-chloro-1- pentene, 3-fluoro-1-pentene, and combinations thereof. In one embodiment, the alkene comprises ethylene, propylene, 1-butene, 2-butene, isobutylene, or combinations thereof. In an embodiment, the alkene comprises ethylene. In another embodiment, the halogenated alkene comprises vinyl chloride, vinylidene chloride, or combinations thereof.

(ii) Halogenated Methane Comprising at Least One Chlorine Atom

A wide variety of halogenated methanes comprising at least one chlorine atom may be used in this process. Non-limiting examples of halogenated methane comprising at least one chlorine atom include methyl chloride, methylene chloride, chloroform, carbon tetrachloride, chlorofluoromethane, dichloromonofluoromethane, trichlorofluoromethane, difluorochloromethane, trifluorochloromethane, bromochloromethane, dibromochloromethane, tribromochloromethane, chloroiodomethane, chlorodiiodomethane, chlorotriiodomethane, bromochlorofluoromethane, bromochlorodifluoromethane, chlorodibromofluoromethane, bromochlorofluoroiodomethane, bromochlorodiiodomethane, and combinations thereof. In an embodiment, the halogenated methane comprising at least one chlorine atom is carbon tetrachloride.

In general, the halogenated methane comprising at least one chlorine atom may be used in excess. Generally, the molar ratio of the halogenated methane comprising at least one chlorine atom to an alkene, a halogenated alkene, or combinations thereof may range from 0.1:1 to about 100:1. In various embodiments, the molar ratio of the halogenated methane comprising at least one chlorine atom to an alkene, a halogenated alkene, or combinations thereof may range from 0.1:1 to about 100:1, from 0.5:1 to about 75:1, from 1:1 to about 10:1, or from 1.2:1 to about 5:1. In various embodiments, the molar ratio of the halogenated methane comprising at least one chlorine atom to an alkene, a halogenated alkene, or combinations thereof may range from 1.2:1 to about 2:1. The halogenated methane comprising at least one chlorine atom and an alkene, a halogenated alkene, or combinations thereof are essentially dry, i.e., it has a water content of the below 1000 ppm. Lower water concentrations are preferred, but not required.

(iii) Ligand

In various embodiments, a ligand may be used in the process. The ligand, as the skilled artisan appreciates, may form a complex with the catalyst, with the resulting complex soluble in the reaction media.

In one embodiment, the ligand comprises a phosphorus containing compound. Examples of phosphorus containing compounds may include trialkylphosphates, trialkylphosphites, or combinations thereof. Suitable non-limiting examples of trialkylphosphates and trialkylphosphite may include triethylphosphate, tripropylphosphate, triisopropylphosphate, tributylphosphate, trimethylphosphite, triethylphosphite, tripropylphosphite, triisopropylphosphite, tributylphosphite, and tri-tertbutylphosphite. In one preferred embodiment, the phosphorus containing compound comprises a trialkylphosphate, namely tributylphosphate.

(iv) Solid Metallic Catalyst

A wide variety of solid metallic catalysts may be used in the process. In some embodiments, the solid metallic catalyst may be a transition metal catalyst. As used herein, the term "transition metal catalyst" refers to a transition metal, i.e., the elemental metal, a transition metal containing alloy, a transition metal salt, or combinations thereof. Transition metals useful in the processes described herein include all transition metals. Non-limiting examples of useful transition metals may be aluminum, chromium, cobalt, copper, iron, titanium, nickel, manganese, tin, antimony, zinc, gold, zirconium, silicon, molybdenum, niobium, tungsten, vanadium, or combinations thereof.

The solid metallic catalyst may be a transition metal containing alloy. Non-limiting examples of metal containing alloys that may be used in the process may be an alloy of aluminum, an alloy of chromium, an alloy of cobalt, an alloy of copper, an alloy of iron, an alloy of titanium, an alloy of nickel, an alloy of manganese, an alloy of tin, an alloy of antimony, an alloy of zinc, an alloy of gold, an alloy of zirconium, an alloy of silicon, an alloy of molybdenum, an alloy of niobium, an alloy of tungsten, an alloy of vanadium, or combinations thereof. Non-limiting common names for these alloys include Al—Li, Alnico, Birmabright, duraluminum, hiduminum, hydroalium, magnalium, Y alloy, nichrome, stellite, ultimet, vitallium, various alloys of brass various alloys of brass, bronze, constantin, Corinthian bronze, cunife, cupronickel, cymbal metals, electrum, haptizon, manganin, nickel silver, Nordic gold, tumbaga, crown gold, colored gold, electrum, rhodite, rose gold, tumbaga, white gold, cast iron, pig iron, Damascus steel, wrought iron, anthracite iron, wootz steel, carbon steel, crucible steel, blister steel, alnico, alumel, brightray, chromel, cupronickel, ferronickel, German silver, Inconel, monel metal, nichrome, nickel-carbon. Nicrosil, nitinol, permalloy, supermalloy, 6al-4v, beta C, gum metal, titanium gold, Babbitt, britannium, pewter, solder, terne, white metal, sterling silver, zamak, zircaloy, or combinations thereof. In a further embodiment, the catalyst is selected from a group consisting of cast iron, pig iron, Damascus steel, wrought iron, anthracite iron, wootz steel, carbon steel, crucible steel, blister steel, and combinations thereof. In a preferred embodiment, the catalyst is iron, an iron alloy, carbon steel, or combinations thereof.

In various embodiments, the at least one solid metallic catalyst may further comprise a transition metal salt, which may be partially or fully dissolved in the liquid phase and may form complexes with the ligand. Non-limiting examples of suitable transition metal salts may include acetates, acetyacetonates, alkoxides, butyrates, carbonyls, dioxides, halides, hexonates, hydrides, mesylates, octanoates, nitrates, nitrosyl halides, nitrosyl nitrates, sulfates, sulfides, sulfonates, phosphates, and combinations thereof. Examples of suitable transition metal salts include, iron (II) chloride, iron (III) chloride, iron (II) bromide, iron (II) iodide, iron (III) bromide, and iron (III) oxide. In an embodiment, the transition metal salt may be iron (II) chloride, iron (III) chloride, or combinations thereof. In a preferred embodiment, the transitional metal salts comprises ferrous chloride, ferric chloride, or combinations thereof.

As appreciated by the skilled artisan, the catalyst, once in the process, may undergo oxidation and/or reduction to produce an activated catalytic species in various oxidation states. The oxidation state of these active iron catalytic species may vary, and include iron having oxidation states of (I), (II), and/or (III). In one aspect, the active iron catalyst may in the Fe(I) oxidation state. In another aspect, the active iron catalyst may be Fe(II). In still another aspect, the active iron catalyst may be in the Fe(III) oxidation state. In an additional aspect, the active iron catalyst may comprise a mixture of Fe(I) and Fe(II). In still another aspect, the active iron catalyst may comprise a mixture of Fe(I) and Fe(III) oxidation states. In yet another aspect, the active iron catalyst may be in the Fe(II) and Fe(III) oxidation states. In another aspect, the active iron catalyst may in the Fe(I), Fe(II) and Fe(III) oxidation states. In still another embodiment, an electrochemical cell may be utilized to adjust the ratio of Fe(I), Fe(II), and Fe(III) in the process. When the ligand is present, it may complex with at least some of the iron metal and/or iron salt present in the reaction.

In various embodiments, the configuration of the at least one solid metallic catalyst may be of various dimensions, shapes, thicknesses, and weights. Non-limiting examples of configurations of the catalyst may be a foil, a screen, a rod, a wire, a ball, a ball bearing, a tube, a ferrule, a nut, a bolt, a nail, a coil, a plate, a sheet, a pipe or combinations thereof. In another embodiment, the catalyst may be suspended within the reaction mixture or affixed to the reactor below the surface of the reaction mixture so the catalyst contacts the reaction mixture. In other embodiments, the catalyst may be part of a fixed bed or a tray.

In various embodiments, the catalyst is in the form of a structured or unstructured packing. Non-limiting examples of structured packing may be Flexipac®, Flexipac HC®, Intalox®, Sulzer®, wire gauze structured packing, or combinations thereof. These structured packing may in various sizes, configurations, and corrugation sizes. Non-limiting examples of corrugation sizes may be extruded, perforated and waffled, perforated and grooved, perforated, smooth, and combinations thereof. Non-limiting examples of unstructured packing may be Flexiring®, Hy-Pak®, IMTP®, Intalox®, Ultra®, or combinations thereof. These unstructured packing may be in various sizes and configurations.

Generally, the surface area of the catalyst may range from 1 $cm^2/(kg/hr)$ to about 10,000 $cm^2/(kg/hr)$. In various embodiments, the surface area of the metal may range 1 $cm^2/(kg/hr)$ to about 10,000 $cm^2/(kg/hr)$, from about 100 $cm^2/(kg/hr)$ to about 7,500 $cm^2/(kg/hr)$, from about 1,000 $cm^2/(kg/hr)$ to about 5,000 $cm^2/(kg/hr)$, or from 2,000 $cm^2/(kg/hr)$ to about 4,000 $cm^2/(kg/hr)$. In one preferred embodiment, the surface area of the metal is 100 to 2500 $cm^2/(kg/hr)$. In another preferred embodiment, the surface area of the metal is or 1750 to 2250 $cm^2/(kg/hr)$. In still another embodiment, the surface area of the metal is 75-425 $cm^2/(kg/hr)$ or 100-350 $cm^2/(kg/hr)$.

Generally, the molar ratio of the at least one solid metallic catalyst to halogenated methane comprising at least one chlorine atom may range from about 0:1 to about 0.1:1. In various embodiments, the molar ratio of the at least one solid metallic catalyst to halogenated methane comprising at least one chlorine atom may range from 0:1 to about 0.1:1, from 0.0001:1 to about 0.05:1, from 0.0025:1 to about 0.01:1, or from 0.005:1 to about 0.008:1. In a preferred embodiment, molar ratio of the at least one solid metallic catalyst to halogenated methane comprising at least one chlorine atom may range from about 0.001:1 to about 0.007:1.

In general, the molar ratio of the dissolved metallic catalyst to the ligand may range from 1:1 to about 1:1000. In various embodiments, the molar ratio of the dissolved metallic catalyst to the ligand may range from 1:1 to about 1:1000, from 1:1 to about 1:500, from 1:1 to about 1:100, or from 1:1 to about 1:10. In one preferred embodiment, the molar ratio of the dissolved dissolved metallic catalyst to the ligand may range from 1:1.5 to about 1:3.

Generally, the molar ratio of the metal salt to the ligand may range from 1:1 to about 1:1000. In various embodiments, the molar ratio of the metal salt to the phosphorus containing compound may range from 1:1 to about 1:1000, from 1:1 to about 1:500, from 1:1 to about 1:100, or from 1:1 to about 1:10. In one preferred embodiment, the molar ratio of the metal salt to the phosphorus containing compound may range from 1:1.5 to about 1:3.

In another embodiment, the at least one solid metallic catalyst in a continuous reactor may be part of a fixed catalyst bed. In still another embodiment, the at least one solid metallic catalyst in a continuous reactor may be part of a cartridge. In still another embodiment, the at least one solid metallic catalyst may be part of a structured or un-structured packing. Using a fixed bed, a cartridge, structured packing, or unstructured packing, the catalyst may be contained and easily replaced.

(v) Introduction of the Catalyst(s) into the Process

Generally, the at least one solid metallic catalyst may be introduced to the process in various ways. In one aspect, the at least one solid metallic catalyst comprising a metal, a metal alloy, a metal salt(s), or combinations thereof may be introduced directly into the process. In another aspect, a catalyst solution comprising at least one solid metallic catalyst may be prepared by dissolving at least a portion of the metal, a metal alloy, metal salt(s), or combinations thereof in a mixture of halogenated methane comprising at least one chlorine atom and the ligand, then adding this solution to the reactor. In yet another embodiment, a catalyst solution may be generated inside the reactor by mixing the metal, a metal alloy, metal salt(s), or combinations thereof, the ligand, and the halogenated methane comprising at least one chlorine atom. As appreciated by the skilled artisan, other methods for introducing the at least one solid metallic catalyst or solution of the at least one catalyst into the reactor may be envisioned. The alkene may be in the reactor before the catalyst is added; the alkene may be added to the reactor after the catalyst, or at the same time.

(b) Reaction Conditions

The processes disclosed herein may be run in a batch mode or a continuous mode, with continuous mode preferred.

In a continuous mode, a stirred tank reactor may be used, or a series of stirred tank reactor to approach the performance of an ideal plug flow reactors may be utilized to improve the overall efficiency of the process. In another embodiment, the process in continuous modes may be stirred in various methods to improve the mixing of the of the reactor components.

As appreciated by the skilled artisan, there are many methods to adequately stir the process. In various embodiments, the liquid phase of the reaction mixture in the reactor may be stirred utilizing jet mixing using at least one nozzle. In other embodiments, jet mixing utilizing at least one eductor may be utilized. In still other embodiments, jet mixing utilizing at least one nozzle and at least one eductor may be utilized. In yet another embodiment, mechanical stirring may be used. In still another embodiment, a combination of all the above methods of stirring may be used.

Jet mixing utilizing at least one nozzle, as appreciated by the skilled artisan, withdraws a portion of the liquid phase of the reaction mixture from the reactor and pumps the liquid phase back into the reactor through at least one nozzle, thereby creating turbulence in the liquid phase. The at least one nozzle may be positioned below the surface of the liquid phase, thereby creating turbulence in the liquid phase and providing increased mixing. The at least one nozzle may be positioned at the surface of the liquid phase or directed through the gas phase into the liquid phase, thereby providing increased turbulence of the reaction mixture but also provides increased absorption of the gas phase into the liquid phase.

Jet mixing utilizing at least one eductor, as appreciated by the skilled artisan, withdraws a portion of the liquid phase of the reaction mixture and pumps the liquid phase back into the reactor through at least one gas educting nozzle. The eductor nozzle provides suction in the eductor which pulls gas from the gas phase of the reaction mixture, mixes the gas with the circulated liquid phase, and returns the resulting mixture of liquid and gas back into the liquid phase of the reactor where the liquid has increased absorption of the gas, as compared to the circulated liquid phase. When the flow from the eductor nozzle is directed towards the liquid phase of the reaction mixture, increased absorption of the gas into the liquid phase, increased turbulence of the reaction mixture, and increased flow through the absorption device results.

Jet mixing may also utilize at least one nozzle and at least one eductor. In this configuration, as described above, not only are increased turbulence in the reaction mixture and increased flow through the absorption device achieved, but increased gas absorption of the gas into the liquid phase is realized.

The use of a spray nozzle may also be utilized. Using a spray nozzle, the liquid phase is pumped through the spray nozzle producing droplets of the liquid phase from the reaction mixture. These droplets may be discharged into the gas phase, where they absorb at least some of the gas phase. The droplets are then reincorporated into the liquid phase of the reaction mixture, thereby increasing the amount of gas dissolved in the liquid phase of the reaction mixture.

In other embodiments, a draft tube may be utilized in the process. The draft tube provides an internal recirculation of the reaction mixture. The circulation may be induced by energy from the at least one liquid jets, from the at least one gas educting nozzle, from rising gas bubbles within the reactor, or a combination thereof.

As appreciated by the skilled artisan, at least one of the methods or a combination of these may be utilized in the process. In a preferred embodiment, jet mixing using at least one eductor nozzle wherein the flow from the eductor nozzle is directed towards the liquid phase of the reaction mixture is utilized.

In general, the process for the preparation of halogenated alkanes will be conducted to maintain the temperature from about 40° C. to about 120° C. using an internal or external heat exchanger. As appreciated by the skilled artisan, the temperature of the reactor is partially maintained by boiling off or vaporizing a portion of the reactants and products. In various embodiments, the temperature of the reaction may be maintained from about 40° C. to about 120° C., from 50° C. to about 110° C., from 60° C. to about 100° C., or from about 70° C. to about 90° C.

Generally, the process may be conducted at a pressure of about 0 psig, 101.3 kPa) to about 200 psi (1379 kPa) so the amount of the gases and liquid are in suitable quantities so the reaction may proceed and maintain the kinetics of the process. In various embodiments, the pressure of the process may be from about atmospheric pressure (~14.7 psi) to about 200 psi, from about 20 psi to about 180 psi, from about 40 psi to about 160 psi, from about 80 psi to about 140 psi, or from 100 psi to about 120 psi.

Generally, the reaction is allowed to proceed for a sufficient period of time until the reaction is complete, as determined by any method known to one skilled in the art, such as chromatography (e.g., GC-gas chromatography). The duration of the reaction may range from about 5 minutes to about 16 hours. In some embodiments, the duration of the reaction may range from about 5 minutes to about 16 hours, from about 1 hour to about 12 hours, from about 2 hours to about 10 hours, from about 4 hours to about 8 hours, or from about 5 hours to about 7 hours.

(c) Output from the Process to Prepare Chlorinated Alkanes in Product Mixture

The processes disclosed herein produce at least one chlorinated alkane and at least one heavy by-product.

Generally, the conversion percentage (%) of the halogenated methane comprising at least one chlorine atom to the chlorinated alkane is at least 50%. In various embodiments, the conversion percentage of the halogenated methane comprising at least one chlorine atom to the chlorinated alkane is at least 50%, at least 60%, at least 70%, at least 80%, at least 90%, or at least 95%.

In general, the process produces the chlorinated alkanes in at least 50 weight percent (wt %) in the product mixture of the reactor. In various embodiments, the chlorinated alkane is produced in at least 50 wt %, in at least 60 wt %, in at least 70 wt %, in at least 80 wt %, in at least 90 wt %, in at least 95 wt %, or in at least 99 wt % in the product mixture of the reactor.

Generally, the process produces chlorinated alkanes and heavy by-products. These heavy by-products are produced in less than 5 weight % in the entire product distribution. In various embodiments, these heavy impurities may be less than 4 weight %, less than 3 weight %, less than 2 weight %, or less than 1 weight %.

In preferred embodiments, the chlorinated alkane is 1,1,1,3-tetrachloropropane; 1,1,1,3,3-pentachloropropane; or 1,1,1,3,3,3-hexachloropropane.

(d) Treatment, Separation, and Recycling of Various Product Steams

After the at least one alkene, halogenated alkene, or combinations thereof is contacted with the a halogenated methane comprising at least one chlorine atom, at least one solid metallic catalyst, and a ligand, a product mixture is formed comprising a chlorinated alkane, light by-products, heavy by-products, and soluble metal ions, complexes of metal ions with the ligand, or combinations thereof. The product mixture does not contain any phase transfer catalyst. At least a portion of this product mixture may undergo various separation steps, treatment steps, or combinations thereof to produce various product mixtures, product effluent streams, treated streams and/or treated mixtures any or all of which may be recycled to the reactor.

In one embodiment, at least a portion of various product mixtures, streams, product effluent streams, heavy fractions, light fractions may undergo at least one separation step. As appreciated by the skilled artisan, many separation techniques or combinations of separation techniques may be useful. Non-limiting examples of separation techniques may be decantation, settling, filtration, centrifugation, thin film evaporation, simple distillation, vacuum distillation, fractional distillation, or a combination thereof. In various embodiments, the at least one of the first separator and the second separator may a distillation column or a multistage distillation column. Additionally, the at least one of the first separator and the second separator may further comprise a reboiler, a bottom stage, or a combination thereof. Various distillation columns may be used in this capacity. In one embodiment, a side draw column or a distillation column which provides outlet stream from an intermediate stage or a dividing wall column (dividing wall column (DWC) is a single shell, fully thermally coupled distillation column capable of separating mixtures of three or more components into high purity products) may be used as a separator. The distillations may comprise at least one theoretical plate.

In another embodiment, at least a portion of various product mixtures, streams, product effluent streams, heavy fractions, light fractions may undergo at least one treatment step. As appreciated by the skilled artisan, the treatment step comprises contacting the at least a portion of various product mixtures, streams, product effluent streams, and/or heavy fractions with an alkaline substance to convert the soluble metal ions, metal ion-ligand complexes, or combinations thereof, to a metal hydroxide. The contacting time with the alkaline substance is sufficient to convert at least a portion of the soluble metal ions, complexes of the metal ions with the ligand, or combinations thereof to a metal hydroxide, where only a small amount or no dehydrochlorination of the chlorinated alkane occurs. The treated mixtures, streams, etc., contain fewer metal ions than the pretreatment mixtures, streams, etc. After treatment, the treated streams may then undergo a separation step to remove the metal hydroxide.

In an embodiment, the alkaline substance may be an aqueous inorganic base. The aqueous base may further contain an inorganic halide salt, e.g., a chloride salt. In an embodiment, the aqueous phase comprising an aqueous base may be produced by the chloroalkali process.

In various embodiments, the inorganic base may be an alkali or alkali earth metal base. Non-limiting examples of these alkali or alkali earth bases may be LiOH, NaOH, KOH, $Ba(OH)_2$, $Ca(OH)_2$, $Na_2CO_3$, $K_2CO_3$, $NaHCO_3$, $KHCO_3$, or combinations thereof. In a preferred embodiment, the alkali or alkali earth metal base may be NaOH, KOH, or combinations thereof. Still more preferably, the base comprises NaOH.

The halide salt may be any alkali or alkali earth metal halide salt, e.g., a chloride salt. Non-limiting examples of these alkali or alkali earth metal salt halide salts may be selected from a group consisting of lithium chloride, sodium chloride, potassium chloride, barium chloride, calcium chloride, or combinations thereof. In a preferred embodiment, the chloride salt comprises sodium chloride. In another embodiment, an aqueous base comprises a mixture of NaOH and at least one chloride salt which was produced from the chloroalkali process through the electrolysis of sodium chloride in a diaphragm cell. In other embodiments, the concentration of the alkali or alkali earth metal halide salt is up to or greater than the saturation limit of the alkali or alkali earth metal halide salt in the inorganic base.

Generally, the concentration of the aqueous base may range from 5 wt % to about 50 wt %. In various embodiments, the concentration of the aqueous base may range from 5 wt % to about 50 wt %, from 7 wt % to about 40 wt %, from 9 wt % to about 30 wt %, or from 10 wt % to about 20 wt %. In a preferred embodiment, the concentration of the aqueous base may range from 5 wt % to about 10 wt %.

In general, the mole ratio of the base(s) to the dissolved and/or complexed metal salts in the various product mixtures may range from 0.1:1.0 to about 2.0:1.0. In various embodiments, the mole ratio of the base(s) to the chlorinated alkane may range from 0.1:1.0 to about 2.0:1.0, from 0.5:1.0 to about 1.5:1.0, or from 0.9:1.0 to about 1.1:1.0. In a preferred embodiment, the mole ratio of the aqueous base to the chlorinated alkane may be about 1.0:1.0.

Generally, the concentration of the halide salt may be up to or below the saturation limit. In various embodiments, the concentration of the halide salt may be greater than 0.01 wt %, greater than 1 wt %, greater than 10 wt %, greater than 20 wt %, at the saturation limit for the suitable halide salt, or below the saturation limit for the suitable halide salt. As is appreciated by the skilled person, the saturation limit depends on the presence of other ions, temperature, pressure, etc.

In an embodiment, the product mixture is distilled to form a distilled product mixture. When the distillation forms only two streams, they are a light fraction (a), and a heavy fraction (b). The light fraction (a) comprises the halogenated methane comprising at least one chlorine atom, the at least one alkene, halogenated alkene, or combinations thereof, light by-products, the chlorinated alkane, and optionally water. The heavy fraction (b) comprises heavy by-products, soluble metal ions, complexes of metal ions with the ligand, or combinations thereof, and the ligand. The heavy fraction (b) is contacted with an aqueous alkaline substance. During this treatment, at least some of the soluble metal ions, the complexes of the metal ions, or combinations thereof react with the base and the metals are converted to a metal hydroxide. This mixture is then transferred to at least one separator where the metal hydroxide is removed. After separation of the metal hydroxide, the treated heavy fraction (c) comprises heavy by-products and the ligand where the treated heavy fraction (c) contains fewer metal ions than heavy fraction (b).

In another embodiment, the product mixture, comprising the chlorinated alkane, light by-products, heavy by-products, soluble metal ions, complexes of metal ions with the ligand, or combinations thereof, is contacted with an aqueous alkaline substance. During this treatment, at least some of the soluble metal ions, complexes of metal ions with the ligand, or combinations are converted to a metal hydroxide. This mixture is then transferred to at least one separator where at least some the metal hydroxide is removed. In one embodiment, as much of the metal hydroxide is removed as possible. After removal of the metal hydroxide, the treated product effluent stream (d) comprises the chlorinated alkane, light by-products, heavy by-products, and the ligand where the treated product stream contains fewer metal ions than the product stream from the process, and optionally water. The treated product effluent stream (d) may be distilled forming a light effluent stream (e) comprising light by-products, the chlorinated alkane, and optionally water and a heavy effluent stream (f) comprising heavy by-products and the ligand.

In order to improve the efficiency of the process, at least a portion of these various separated mixtures, streams, treated streams, separated fractions, and treated fractions may be recycled to the reactor. In various embodiments, at least a portion of the light fraction (a) comprising the chlorinated alkane and light by-products, treated heavy fraction (c) comprising heavy by-products and the ligand, the treated product effluent stream (d) comprising the chlorinated alkane, light by-products, heavy by-products, and the ligand, light effluent stream (e) comprising light by-products and the chlorinated alkane, the heavy effluent stream (f) comprising the heavy by-products and the ligand, or combinations thereof may be recycled, entirely or in part, to the process in the reactor, as described above.

In another embodiment, at least a portion of light fraction (a), treated heavy fraction (c), product effluent stream (d), light effluent stream (e), heavy effluent stream (f), or combinations thereof may be mixed with fresh material feeds before being recycled back into the reactor in batch mode or continuous mode, where the fresh material feeds comprise a halogenated methane comprising at least one chlorine atom, an alkene, halogenated alkene, or combinations thereof, the at least one ligand, or combinations thereof. In other embodiments, the fresh material feed may be added to the reactor. The introduction of these fresh material feeds or mixing the fresh material feeds with at least a portion of the recycle light fraction (a), treated heavy fraction (c), product effluent stream (d), light effluent stream (e), heavy effluent stream (f), or combinations increases the efficiency of the process, reduces the overall cost, maintains the kinetics, increase the through-put, and reduces the by-products produced by the process. The amounts of the recycle light fraction (a), treated heavy fraction (c), product effluent stream (d), light effluent stream (e), heavy effluent stream (f), or combinations or fresh material feed streams added to the reactor may be the same or different. One way to measure the amount of the recycle light fraction (a), treated heavy fraction (c), product effluent stream (d), light effluent stream (e), heavy effluent stream (f), or combinations or fresh material feed streams being added to the reactor is to identify the mass flow of each of these streams. The recycle light fraction (a), treated heavy fraction (c), product effluent stream (d), light effluent stream (e), heavy effluent stream (f), or combinations being recycled to the reactor have a recycle product effluent mass flow, while the fresh material feed streams being added to the reactor has a fresh material feed mass flow. Mass flows may be measured using methods known in the art.

Generally, the mass ratio of the product effluent stream mass flow being recycled to the fresh material feed mass flow is adjusted to maintain the conversion of the process and/or maintain the kinetics of the process.

The chlorinated alkane contained in light fraction (a), product effluent stream (d), light effluent stream (e) may have a yield of at least about 20%. In various embodiments, the chlorinated alkane contained in light fraction (a), product effluent stream (d), or light effluent stream (e) may have a yield of at least about 20%, at least about 50%, at least about 70%, at least about 75%, at least about 80%, at least about 85%, at least about 90%, at least about 95%, or at least about 99%.

The chlorinated alkane contained in in light fraction (a), product effluent stream (d), or light effluent stream (e) from the process may have a weight percent at least about 50%, at least about 60%, at least about 65%, at least about 70%, at least about 75%, at least about 80%, at least about 85%, at least about 90%, at least about 95%, at least about 99%, at least about 99.5%, or at least about 99.9%.

(e) Separation and Purification of the Chlorinated Alkane

The next step in the process comprises separating the chlorinated alkane from at least a portion of light fraction (a), product effluent stream (d), light effluent stream (e), or combinations thereof. Depending on the purity of the chlorinated alkane from the process, further components may be the alkene, the chlorinated alkene, or combinations thereof, the halogenated methane comprising at least one chlorine atom, the ligand, and optionally water. In a preferred embodiment, the chlorinated alkane is 1,1,1,3-tetrachloropropane. In another preferred embodiment, the chlorinated alkane is 1,1,1,3,3-pentachloropropane. In still another preferred embodiment, the chlorinated alkane is 1,1,1,3,3,3-hexachloropropane.

The separation process commences by transferring at least a portion of light fraction (a), product effluent stream (d), light effluent stream (e), or combinations thereof to at least one separator and alternatively a second separator in order to isolate the chlorinated alkane in the desired yield and/or purity. In various embodiments, the at least one of the first separator and the second separator may be a distillation column or a multistage distillation column. Additionally, the at least one of the first separator and the second separator may further comprise a reboiler, a bottom stage, or a combination thereof. Various distillation columns may be used in this capacity. In one embodiment, a side draw column or a distillation column which provides an outlet stream from an intermediate stage or a divided wall column may be used as a separator.

Separating the purified chlorinated alkane comprising either the light fraction (a) or the light effluent stream (e) would produce at least two product streams. Separating the chlorinated alkane comprising the product effluent stream (d) would produce at least three product streams. In various embodiments, separating the purified chlorinated alkene may produce three, four, or more product streams depending on the separation device utilized and the purity of the chlorinated alkane.

Generally, a portion of the light fraction (a), the light effluent stream (e), or combinations thereof may be distilled to produce two product effluent streams, product effluent stream (i) and (ii). Product effluent stream (i) comprises light by-products such as the halogenated methane comprising at least one chlorine atom and the at least one alkene, chlorinated alkene, or combinations thereof while product effluent stream (ii) comprises the chlorinated alkane. For added efficiency, product effluent stream (i) may be recycled to the reactor or another process.

In general, at least a portion of product effluent stream (d) may be distilled to produce at least three product streams, product effluent streams (iii), (iv), and (v). Product effluent stream (iii) comprises light by-products such as the halogenated methane comprising at least one chlorine atom and the at least one alkene, chlorinated alkene, or combinations thereof, product effluent stream (iv) comprises the chlorinated alkane, and product effluent stream (v) comprises the heavy by-products and the ligand. For added efficiency, product effluent stream (iii) and (v) may be recycled to the reactor or another process.

In yet another embodiment, at least a portion of product effluent stream (ii) and (iv) comprising the chlorinated alkane may be transferred into an additional separation device to achieve the desired purity of the chlorinated alkane.

The process as described above may yield the chlorinated alkane in at least 20%. In various embodiments, the process as described above may have a yield of at least 20%, at least 30%, at least 40%, at least 50%, at least 60%, at least 75%, at least 85%, at least 95%, and at least 99%.

The chlorinated alkane produced from the process may have a weight percent at least about 50%. In various embodiments, the chlorinated alkane produced in the process may have a weight percent of at least 50%, at least about 60%, at least about 65%, at least about 70%, at least about 75%, at least about 80%, at least about 85%, at least about 90%, at least about 95%, at least about 99%, at least about 99.5%, or at least about 99.9%.

(II) Preferred Embodiment: Process for Preparing of 1,1,1,3-Tetrachloropropane (a) Reaction Mixture In another aspect, disclosed herein are processes to prepare 1,1,1,3-tetrachloropropane. The process commences by preparing a reaction mixture in a reactor comprising ethylene, carbon tetrachloride, at least one solid metallic catalyst, and a ligand. The at least one solid metallic catalyst is described in Section (I)(a)(iv) and the ligand is described in Section (I)(a)(iii). In preferred embodiments, the solid metallic catalyst comprises ferric chloride and the ligand is tributylphosphate.

(b) Reaction Conditions

The reaction conditions are described above in Section (I)(b).

(c) Output from the Process to Prepare Chlorinated Alkanes in Product Mixture

The output to produce the chlorinated alkane from the process outlined above is described above in Section (I)(c).

The process, as outlined above, produces 1,1,1,3-tetrachloropropane and heavy by-products in the product mixture. Generally, the conversion percentage (%) of the carbon tetrachloride to 1,1,1,3-tetrachloropropane is at least 50%. In various embodiments, the conversion percentage of the carbon tetrachloride to 1,1,1,3-tetrachloropropane is at least 50%, at least 60%, at least 70%, at least 80%, at least 90%, or at least 95%.

In general, the process produces 1,1,1,3-tetrachloropropane in at least 50 weight percent (wt %) in the product mixture of the reactor. In various embodiments, 1,1,1,3-tetrachloropropane is produced in at least 50 wt %, in at least 60 wt %, in at least 70 wt %, in at least 80 wt %, in at least 90 wt %, in at least 95 wt %, or in at least 99 wt % in the product mixture of the reactor.

Generally, the process produces 1,1,1,3-tetrachloropropane and heavy by-products. These heavy by-products are produced in less than 5 weight % in the entire product distribution. In various embodiments, these heavy by-products may be less than 4 weight %, less than 3 weight %, less than 2 weight %, or less than 1 weight %.

(d) Treatment, Separation, and Recycling of Various Product Steams

The treatment, separation, and recycling of various product streams is described above in Section (I)(d).

(e) Separation and Purification of 1,1,1,3-tetrachloropropane.

The separation and purification of 1,1,1,3-tetrachloropropane is described above in Section (I)(e).

The 1,1,1,3-tetrachloropropane produced from the process may have a yield at least about 20%. In various embodiments, the 1,1,1,3-tetrachloropropane produced in the process may have a yield of at least 20%, at least about 40%, at least about 60%, at least about 70%, at least about 75%, at least about 80%, at least about 85%, at least about 90%, at least about 95%, at least about 99%, at least about 99.5%, or at least about 99.9%.

The 1,1,1,3-tetrachloropropane produced from the process may have a weight percent at least about 50%. In various embodiments, the 1,1,1,3-tetrachloropropane produced in the process may have a weight percent of at least 50%, at least about 60%, at least about 65%, at least about 70%, at least about 75%, at least about 80%, at least about 85%, at least about 90%, at least about 95%, at least about 99%, at least about 99.5%, or at least about 99.9%.

(III) Preferred Embodiment: Process for Preparing of 1,1,1,3,3-Pentachloropropane (a) Reaction Mixture In another aspect, disclosed herein are processes to prepare 1,1,1,3,3-pentachloropropane. The process commences by preparing a reaction mixture in a reactor comprising vinyl chloride, carbon tetrachloride, at least one solid metallic catalyst, and a ligand. The solid metallic catalyst is described in Section (I)(a)(iv) and the ligand is described in Section (I)(a)(iii). In preferred embodiments, the solid metallic catalyst comprises ferric chloride and the ligand is tributylphosphate.

(b) Reaction Conditions

The reaction conditions are described above in Section (I)(b).

(c) Output from the Process to Prepare Chlorinated Alkanes in Product Mixture

The output to produce the 1,1,1,3,3-pentachloropropane from the process outlined above is described above in Section (I)(c).

The process, as outlined above, produces 1,1,1,3,3-pentachloropropane and heavy by-products in the product mixture. Generally, the conversion percentage (%) of the carbon tetrachloride to 1,1,1,3,3-pentachloropropane is at least 50%. In various embodiments, the conversion percentage of the carbon tetrachloride to 1,1,1,3,3-pentachloropropane is at least 50%, at least 60%, at least 70%, at least 80%, at least 90%, or at least 95%.

In general, the process produces the 1,1,1,3,3-pentachloropropane in at least 50 weight percent (wt %) in the product mixture of the reactor. In various embodiments, 1,1,1,3,3-pentachloropropane is produced in at least 50 wt %, in at least 60 wt %, in at least 70 wt %, in at least 80 wt %, in at least 90 wt %, in at least 95 wt %, or in at least 99 wt % in the product mixture of the reactor.

Generally, the heavy by-products are produced in less than 5 weight % in the entire product distribution. In various embodiments, these heavy by-products may be less than 4 weight %, less than 3 weight %, less than 2 weight %, or less than 1 weight %.

(d) Treatment, Separation, and Recycling of Various Product Steams

The treatment, separation, and recycling of various product streams is described above in Section (I)(d).

(e) Separation and Purification of 1,1,1,3,3-pentachloropropane

The separation and purification of 1,1,1,3,3-pentachloropropane is described above in Section (I)(e).

The 1,1,1,3,3-pentachloropropane produced from the process may have a yield at least about 20%. In various embodiments, the 1,1,1,3,3-pentachloropropane produced in the process may have a yield of at least 20%, at least about 40%, at least about 60%, at least about 70%, at least about 75%, at least about 80%, at least about 85%, at least about 90%, at least about 95%, at least about 99%, at least about 99.5%, or at least about 99.9%.

The 1,1,1,3,3-pentachloropropane produced from the process may have a weight percent at least about 50%. In various embodiments, the 1,1,1,3,3-pentachloropropane produced in the process may have a weight percent of at least 50%, at least about 60%, at least about 65%, at least about 70%, at least about 75%, at least about 80%, at least about 85%, at least about 90%, at least about 95%, at least about 99%, at least about 99.5%, or at least about 99.9%.

(IV) Preferred Embodiment: Process for Preparing of 1,1,1,3,3,3-Hexachloropropane (a) Reaction Mixture In another aspect, disclosed herein are processes to prepare 1,1,1,3,3,3-hexachloropropane. The process commences by preparing a reaction mixture in a reactor comprising vinylidene chloride, carbon tetrachloride, at least one solid metallic catalyst, and a ligand. The solid metallic catalyst is described in Section (I)(a)(iv) and the ligand is described in Section (I)(a)(iii). In preferred embodiments, the solid metallic catalyst comprises ferric chloride and the ligand is tributylphosphate.

(b) Reaction Conditions

The reaction conditions are described above in Section (I)(b).

(c) Output from the Process to Prepare Chlorinated Alkanes in Product Mixture

The output to produce the 1,1,1,3,3,3-hexachloropropane from the process outlined above is described above in Section (I)(c).

The process, as outlined above, produces 1,1,1,3,3,3-hexachloropropane and heavy by-products in the product mixture. Generally, the conversion percentage (%) of the carbon tetrachloride to 1,1,1,3,3,3-hexachloropropane is at least 50%. In various embodiments, the conversion percentage of the carbon tetrachloride to 1,1,1,3,3,3-hexachloropropane is at least 50%, at least 60%, at least 70%, at least 80%, at least 90%, or at least 95%.

In general, the process produces the 1,1,1,3,3,3-hexachloropropane in at least 50 weight percent (wt %) in the product mixture of the reactor. In various embodiments, 1,1,1,3,3,3-hexachloropropane is produced in at least 50 wt %, in at least 60 wt %, in at least 70 wt %, in at least 80 wt %, in at least 90 wt %, in at least 95 wt %, or in at least 99 wt % in the product mixture of the reactor.

Generally, the process produces 1,1,1,3,3,3-hexachloropropane and heavy by-products. These heavy by-products are produced in less than 5 weight % in the entire product distribution. In various embodiments, these heavy by-products may be less than 4 weight %, less than 3 weight %, less than 2 weight %, or less than 1 weight %.

(d) Treatment, Separation, and Recycling of Various Product Steams

The treatment, separation, and recycling of various product streams is described above in Section (I)(d).

(e) Separation and Purification of 1,1,1,3,3,3-hexachloropropane.

The separation and purification of 1,1,1,3,3,3-hexachloropropane is described above in Section (I)(e).

The 1,1,1,3,3,3-hexachloropropane produced from the process may have a yield at least about 20%. In various embodiments, the 1,1,1,3,3,3-hexachloropropane produced in the process may have a yield of at least 20%, at least about 40%, at least about 60%, at least about 70%, at least about 75%, at least about 80%, at least about 85%, at least about 90%, at least about 95%, at least about 99%, at least about 99.5%, or at least about 99.9%.

The 1,1,1,3,3,3-hexachloropropane produced from the process may have a weight percent at least about 50%. In various embodiments, the 1,1,1,3,3,3-hexachloropropane produced in the process may have a weight percent of at least 50%, at least about 60%, at least about 65%, at least about 70%, at least about 75%, at least about 80%, at least about 85%, at least about 90%, at least about 95%, at least about 99%, at least about 99.5%, or at least about 99.9%.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples illustrate various embodiments of the invention.

Example 1: Test Production of 1,1,1,3-Tetrachloropropane in a Batch Autoclave with Recycle of Heavies Containing TBP and Fe-TBP Complex The following protocol was designed to test production of 1,1,1,3-tetrachloropropane (250 fb) in the lab by reaction of carbon tetrachloride (Tet) and ethylene in the presence of iron metal, FeCl$_3$ and tributyl phosphate (TBP) in an autoclave with about 15 cc liquid volume. The autoclave was prepared by adding 30.5 cm×1.2 mm diameter iron wire coiled in the bottom. A stock solution of 10% FeCl$_3$, 17.5% TBP and 72.5% Tet by weight was prepared. For the baseline run 16.4 g Tet, 0.367 g stock solution and 1.867 g heavies from distilling the crude product from previous runs were added to a vial and mixed. The heavies still contained soluble Fe and TBP from the previous runs. The distillation was performed by washing the crude product into a flask with Tet, then heating and purging the flask with nitrogen to effect vaporization of most of the Tet, 250 fb and other light components at low temperature (<110° C.). The liquid reactants were poured into the autoclave, the autoclave was sealed, and stirring was started at 300 rpm. The autoclave was purged with nitrogen two times and purged with ethylene three times (with stirring to help remove some inerts and trace water from the liquid reactants.) Then, the autoclave was padded with ethylene to 120 psig, and the ethylene feed was closed. The autoclave was heated to 100° C., then the ethylene feed valve was opened and the pressure was set to 120 psig. An initial sample of 1.273 g was taken for iron analysis, and then subsequent smaller samples were taken as the reaction progressed for GC analysis. After 3 hours, the heat was turned off, the system was cooled to below 35° C., the ethylene was turned off, and the system was vented. Table 1 shows the results. The total TBP added was estimated based on the amount from the stock solution plus the amount that had been added to the runs from which the TBP was recycled.

Example 2: Test Production of 1,1,1,3-Tetrachloropropane in a Batch Autoclave with Recycle of Heavies Containing TBP and Fe-TBP Complex after a Portion of the Fe was Removed by Treatment with Aqueous NaOH Example 1 was repeated using the same amount of the same crude product from earlier runs. Prior to distillation, the crude product was shaken in a vial with 2.87 g of an aqueous solution containing 8% NaOH and 16% NaCl by weight. The treated crude product was separated from the aqueous phase. The distillation of the treated crude product mixture was more effective than example 1 (more of the lights, Tet and 1,1,1,3-tetrachloropropane distilled overhead), resulting in a smaller amount of heavies added to the autoclave, but none of the Fe and TBP contained in the treated or untreated crude was lost in distillation in either example.

Table 1 shows that Run 2, in which the crude product from earlier runs was treated to remove some of the iron prior to distillation and addition to the reaction, exhibited higher conversion (faster kinetics) compared to Run 1, in which the crude product was not treated. Selectivity of each run were essentially the same. The FIGURE shows the same effects graphically. In the FIGURE, additional curves in which no catalyst components were recycled and in which the crude product from earlier runs was treated with ion exchange resin prior to distillation and addition to the reaction are also shown for comparison.

TABLE 1

Comparison between Run 1 and Run 2

|  | Run 1 Baseline | Run 2 NaOH Treated |
|---|---|---|
| Tet Added (g) | 16.4 | 16.2 |
| Heavies Added (g) | 1.867 | 0.835 |
| FeCl$_3$ added with stock solution (g) | 0.036 | 0.037 |
| TBP added with stock solution (g) | 0.064 | 0.065 |
| Total FeCl$_3$ Added (g) | 0.125 | 0.048 |
| Total TBP Added (g) | 0.305 | 0.304 |
| Excess TBP (g) | 0.099 | 0.225 |
| FeClx/TBP Molar Ratio | 0.675 | 0.259 |
| Conv @ 2 Hrs (%) | 54.5 | 89 |
| Selectivity @ 2 Hrs (%) | 97.3 | 96.8 |
| Final Conv. (%) | 76.9 | 92.5 |
| Final Select. (%) | 96.9 | 96.7 |
| Final Time (Hr) | 3 | 2.58 |
| Initial Total Fe ppm | 2632 | 1019 |
| Final Total Fe ppm | 3192 | 2654 |
| Tot. Liq. Recov. (g) | 16.72 | 16.43 |

What is claimed is:

1. A process for producing a chlorinated alkane, the process comprising:
   (a) contacting at least one alkene, chlorinated alkene, or combinations thereof, a halogenated methane comprising at least one chlorine atom, at least one solid metallic catalyst, and at least one ligand to form a reaction mixture in a reactor;
   (b) forming a product mixture comprising a chlorinated alkane, light by-products, heavy by-products, soluble metal ions, complexes of metal ions with the at least one ligand, or combinations thereof;
   (c) optionally distilling at least a portion of the product mixture to form a light fraction and a distilled product mixture comprising the heavy by-products, soluble metal ions and complexes of metal ions with the at least one ligand;
   (d) treating at least a portion of the product mixture from step (b) and/or the distilled product mixture from step (c) with an alkaline substance in the absence of a phase transfer catalyst, to form a treated product mixture and/or treated distilled product mixture; wherein the alkaline substance is insoluble in the treated product mixture or the treated distilled product mixture; wherein the alkaline substance reacts with at least some of the metal ions that are present and forms a metal hydroxide; and wherein the treated product mixture and/or the treated distilled product mixture contains fewer metal ions and/or complexes of metal ions with the at least one ligand than the product mixture from step (b); and
   (e) separating the metal hydroxide from the treated product mixture and/or the treated distilled product mixture to form a treated product effluent stream and/or a treated distilled effluent stream.

2. The process of claim 1 further comprising step (f) distilling the treated product effluent stream and/or the treated distilled effluent stream of step (e) to form the final treated product stream and/or the final treated distilled product stream.

3. The process of claim 2, further comprising:
   step (g) recycling a portion of at least one of the light fraction from step (c), the distilled product mixture from step (c), treated product effluent stream and/or a treated distilled effluent stream from step (e), the final treated product stream and/or the final treated distilled product stream from step (f), to the reactor.

4. The process of claim 3, wherein the treated product effluent stream from step (e), the treated distilled effluent stream from step (e), and the final treated product stream and/or the final treated distilled product stream from step (f) contains fewer metal ions and/or complexes of metal ions with the at least one ligand than the product mixture from step (b) and further comprises the at least one ligand, and wherein at least a portion of at least one of treated product effluent stream from step (e), the treated distilled effluent stream from step (e), and the final treated product stream and/or the final treated distilled product stream from step (f) is recycled to the reactor.

5. The process of claim 3, wherein a portion of at least one of the distilled product mixture from step (c), treated product effluent stream from step (e), the treated distilled effluent stream from step (e), the final treated product stream from step (f), the final treated distilled product stream from step (f), or combinations thereof is dried prior to recycling to the reactor.

6. The process of claim 1, wherein the chlorinated alkane comprises 1,1,1,3-tetrachloropropane (250FB); 1,1,1,3,3-pentachloropropane (240FA); 1,1,1,3,3,3-hexachloropropane, or combinations thereof.

7. The process of claim 1, wherein the halogenated methane comprising at least one chlorine atom comprises carbon tetrachloride.

8. The process of claim 1, wherein the alkene comprises ethylene.

9. The process of claim 1, wherein the halogenated alkene comprises vinyl chloride, vinylidene chloride, or combinations thereof.

10. The process of claim 1, wherein the at least one solid metallic catalyst comprises a metal, a metal alloy, a salt of the metal, a metal powder, or combinations thereof.

11. The process of claim 1, wherein the at least one solid metallic catalyst is selected from the group consisting of aluminum, bismuth, chromium, cobalt, copper, gallium, gold, indium, iron, lead, magnesium, manganese, mercury, nickel, platinum, palladium, rhodium, samarium, scandium, silver, titanium, tin, zinc, zirconium, and combinations thereof.

12. The process of claim 1, wherein the at least one solid metallic catalyst comprises iron metal, an iron containing compound, an iron containing alloy, an iron salt, or combinations thereof.

13. The process of claim 1, wherein the at least one solid metallic catalyst complexes with the at least one ligand to form an active catalytic species.

14. The process of claim 13, wherein the active catalytic species comprises Fe(0), Fe(II), Fe(III), or combinations thereof.

15. The process of claim 1, wherein the at least one ligand comprises at least one trialkylphosphate, at least one trialkylphosphite, or combinations thereof.

16. The process of claim 15, wherein the trialkylphosphate comprises triethylphosphate, tripropylphosphate, triisopropylphosphate, tributylphosphate, or combinations thereof.

17. The process of claim 15, wherein the trialkylphosphite comprises trimethylphosphite, triethylphosphite, tripropylphosphite, triisopropylphosphite, tributylphosphite, tri-tert-butylphosphite, or combinations thereof.

18. The process of claim 1, wherein the alkaline substance comprises a solid inorganic hydroxide, an aqueous solution comprising an inorganic hydroxide, aqueous ammonia, or combinations thereof.

19. The process of claim 18, wherein the alkaline substance is an inorganic hydroxide, and wherein the inorganic hydroxide comprises lithium hydroxide, sodium hydroxide, potassium hydroxide, barium hydroxide, or combinations thereof.

20. The process of claim 18, wherein the weight % of the alkaline substance in the aqueous solution is less than 20%.

21. The process of claim 20, wherein the aqueous phase comprising an inorganic hydroxide further comprises up to a 26 wt % of a chloride salt selected from the group consisting of lithium chloride, sodium chloride, potassium chloride, barium chloride, calcium chloride, and combinations thereof.

22. The process of claim 21, wherein the chloride salt is sodium chloride.

23. The process of claim 1, wherein the temperature of the process ranges from 40° C. to 120° C.

24. The process of claim 1, wherein the pressure of the process ranges from 0 psig to 200 psig.

25. The process of claim 1, wherein the process is batch or continuous.

26. The process of claim 1, wherein the weight % of the halogenated alkane is at least 50 weight % in the product mixture.

27. The process of claim 1, wherein the conversion % of the halogenated methane comprising at least one chlorine atom to the halogenated alkane is at least 50%.

28. The process of claim 1, wherein the chlorinated alkane is converted into a fluorinated product.

29. The process of claim 1, wherein the product mixture is distilled after step b) and prior to step c); wherein a top stream comprising at least a portion of the alkene, chlorinated alkene, or combinations thereof, and the halogenated methane comprising at least one chlorine atom, and a bottom stream are formed and at least a portion of the top stream is recycled to the reactor; and at least a portion of the bottom stream is used in step c) and/or step d).

30. A process for producing 1,1,1,3-tetrachloropropane, 1,1,1,3,3-pentachloropropane or 1,1,1,3,3,3-hexachloropropane comprising:
a) contacting ethylene, vinyl chloride or 1,1-dichloroethylene, respectively, with carbon tetrachloride, at least one solid metallic catalyst, and a ligand to form a reaction mixture, in a reactor;
b) forming a product mixture comprising light by-products, heavy by-products and soluble metal ions, complexes of metal ions with the ligand, or combinations thereof, and at least one of 1,1,1,3-tetrachloropropane, 1,1,1,3,3-pentachloropropane or 1,1,1,3,3,3-hexachloropropane;
c) optionally distilling at least a portion of the product mixture forming a heavy fraction and a light fraction, the light fraction comprising light by-products and at least one of 1,1,1,3-tetrachloropropane, 1,1,1,3,3-pentachloropropane or 1,1,1,3,3,3-hexachloropropane;
d) treating at least a portion of the product mixture from step (b) or a heavy fraction from distillation from step (c) with an alkaline substance in the absence of a phase transfer catalyst, to form a treated product mixture or treated heavy fraction stream; wherein the alkaline substance is insoluble in the treated product mixture or the treated heavy fraction stream; wherein the alkaline substance reacts with at least some of the metal ions and forms a metal hydroxide; and wherein the treated product mixture or the treated heavy fraction stream contains fewer metal ions than the product mixture;
e) separating the metal hydroxide from the treated product mixture or the heavy fraction to form a treated product effluent stream or the treated heavy fraction stream; and
f) optionally distilling the treated product effluent stream from step (e) and thereby forming at least a light effluent stream and a heavy effluent stream; and
g) recycling a portion of the light fraction from step (c), treated product effluent stream from step (e), the treated heavy fraction stream from step (e), the light effluent stream from step (f), heavy effluent stream from step (f), or combinations thereof to the reactor.

31. The process of claim 30, wherein the treating at least a portion of the product mixture from step (b) with the alkaline substance is carried out in the absence of a phase transfer catalyst.

* * * * *